(12) United States Patent
Weede et al.

(10) Patent No.: US 12,727,943 B2
(45) Date of Patent: Sep. 8, 2026

(54) TECHNIQUE FOR GUIDING A SURGEON ON HOW TO ADAPT A PRE-PLANNED POSITION OF AT LEAST ONE IMPLANT INTERFACE

(71) Applicant: Stryker European Operations Limited, Carrigtwohill (IE)

(72) Inventors: Oliver Weede, Freiburg (DE); Markus Finke, Berlin (DE); Maria Manuel Carvalho de Freitas Martins, Eguisheim (FR)

(73) Assignee: Stryker European Operations Limited, Carrigtwohill (IE)

( * ) Notice: Subject to any disclaimer, the term of this patent is extended or adjusted under 35 U.S.C. 154(b) by 482 days.

(21) Appl. No.: 18/143,146

(22) Filed: May 4, 2023

(65) Prior Publication Data

US 2023/0363823 A1 Nov. 16, 2023

(30) Foreign Application Priority Data

May 12, 2022 (EP) .................................... 22173003

(51) Int. Cl.
*A61B 34/10* (2016.01)
*A61B 34/00* (2016.01)

(52) U.S. Cl.
CPC .............. *A61B 34/10* (2016.02); *A61B 34/25* (2016.02); *A61B 2034/105* (2016.02); *A61B 2034/107* (2016.02); *A61B 2034/252* (2016.02)

(58) Field of Classification Search
CPC ........ A61B 2034/105; A61B 2034/107; A61B 2034/108; A61B 17/7002–7031
See application file for complete search history.

(56) References Cited

U.S. PATENT DOCUMENTS 10,130,430 B2 11/2018 Kao et al.
10,154,239 B2 12/2018 Casas
(Continued)

FOREIGN PATENT DOCUMENTS

EP 1523950 A1 4/2005
WO 2017151904 A1 9/2017
(Continued)

OTHER PUBLICATIONS

Weede, J. et al., "Knowledge-Based Planning of Port Positions for Minimally Invasive Surgery", IEEE Conference on Cybernetics and Intelligent Systems (CIS), 2013, pp. 12-17.

*Primary Examiner* — David W Bates
(74) *Attorney, Agent, or Firm* — Howard & Howard Attorneys PLLC

(57) ABSTRACT

A method for guiding a surgeon on how to adapt a pre-planned position of an implant interface. The implant interface is configured to couple to an implant connector configured to connect the implant interface with an implant interface of another implant. The method is performed by a processing system and comprises obtaining a pre-planned position of an implant interface, obtaining reference positions of the implant interface, determining a deviation between the pre-planned position and the reference positions, and triggering display of a visualization comprising an indication of the deviation to guide a surgeon on how to adapt the pre-planned position of the implant interface. A system and a computer program are also described.

19 Claims, 7 Drawing Sheets

(56) References Cited

U.S. PATENT DOCUMENTS

| | | | | |
|---|---|---|---|---|
| 10,390,886 | B2 | 8/2019 | Li et al. | |
| 10,594,998 | B1 | 3/2020 | Casas | |
| 12,471,998 | B2 * | 11/2025 | O'Connor | A61B 34/10 |
| 2005/0085714 | A1 * | 4/2005 | Foley | A61B 17/7089 600/424 |
| 2008/0319448 | A1 | 12/2008 | Lavallee et al. | |
| 2009/0254326 | A1 | 10/2009 | Isaacs | |
| 2015/0250553 | A1 | 9/2015 | Jaramaz et al. | |
| 2016/0235480 | A1 * | 8/2016 | Scholl | A61B 34/10 |
| 2016/0242857 | A1 | 8/2016 | Scholl | |
| 2023/0076677 | A1 * | 3/2023 | Herrmann | A61B 17/7002 |
| 2024/0299095 | A1 * | 9/2024 | Widmer | A61B 17/7092 |

FOREIGN PATENT DOCUMENTS

| | | | |
|---|---|---|---|
| WO | 2020102761 | A1 | 5/2020 |
| WO | 2020105049 | A1 | 5/2020 |
| WO | 2021007418 | A2 | 1/2021 |
| WO | 2021225840 | A1 | 11/2021 |

* cited by examiner

L5
L4
L3
L2
48
L1

L5
L4
L3
L2
48
L1

L5
L4
L3
L2
48
L1

TECHNIQUE FOR GUIDING A SURGEON ON HOW TO ADAPT A PRE-PLANNED POSITION OF AT LEAST ONE IMPLANT INTERFACE

PRIORITY CLAIM

This application claims priority under 35 U.S.C. § 119 to European Patent Application No. 22173003.9, filed May 12, 2022, the entire contents of which are hereby incorporated by reference.

TECHNICAL FIELD

The present disclosure generally relates to a method for guiding a surgeon on how to adapt a pre-planned position of at least one implant interface, wherein the at least one implant interface is configured to couple to an implant connector configured to connect the at least one implant interface with an implant interface of another implant. The present disclosure also provides for a corresponding processing system and computer program.

BACKGROUND

In computer-assisted surgery (CAS), positions of implants may be pre-planned before a surgical procedure for implanting the implants is performed.

Some implants comprise an implant interface configured to couple to an implant connector. The implant connector is configured to connect implants to one another via the implant interfaces of the respective implants. The implant connector may thus impose spatial restrictions on the placement of the implants.

Current solutions may use pre-planned implant positions that contradict the spatial restrictions imposed by the implant connector. In consequence, when placing the implants at the pre-planned implant positions, it may not be possible to connect the implant connector to the implant interfaces of the placed implants, or the implant connector may need to be reshaped to couple to all implant interfaces. In some cases, the surgeon may couple the implant connector to the implant interfaces by moving the implants that were placed without considering the spatial restrictions imposed by the implant connector. This may result in movements of placed implants that lead to anatomical deformations detrimental to the surgical outcome.

SUMMARY

There is a need for a technique that solves one or more of the above or other problems.

According to a first aspect, a method for guiding a surgeon on how to adapt a pre-planned position of at least one implant interface is provided. The at least one implant interface (e.g., being part of a first implant) is configured to couple to an implant connector configured to connect the at least one implant interface with an implant interface of another (e.g., a second) implant. The method is performed by a processing system and comprises obtaining interface data indicative of a pre-planned position of at least one implant interface, and obtaining reference data indicative of one or more reference positions of the at least one implant interface. The method further comprises determining, based on the interface data and the reference data, a deviation between the pre-planned position of the at least one implant interface and the one or more reference positions. The method comprises triggering display of a visualization comprising an indication of the deviation or of information derived from the deviation, to guide a surgeon on how to adapt the pre-planned position of the at least one implant interface.

The method is performed by a processing system and, thus, may be referred to as a computer-implemented method. The method does not include a surgical step.

The deviation may be indicative of a spatial relationship between the pre-planned position of the at least one implant interface and exactly one of the one or more reference positions.

The deviation may comprise or be a distance between the pre-planned position of the at least one implant interface and the exactly one of the one or more reference positions.

The deviation may comprise or be a distance between a projection of the pre-planned position of the at least one implant interface into a predefined plane and a projection of the exactly one of the one or more reference positions into the predefined plane. The deviation may comprise or be a minimum distance among all distances between the projection of the pre-planned position into the predefined plane and projections of the one or more reference positions into the predefined plane. The predefined plane may correspond to a coronal plane of a patient's body or to a plane parallel to the coronal plane. Alternatively, the predefined plane may correspond to a sagittal plane of the patient's body or to a plane parallel to the sagittal plane.

The deviation may comprise or be a smallest distance of distances between the pre-planned position of the at least one implant interface and the one or more reference positions.

The reference data may be indicative of a curve or volume defining the one or more reference positions. The one or more reference positions may lie on the curve or within the volume.

The one or more reference positions may be specific for the implant connector. The curve or volume may correspond to a shape of the implant connector. The volume may define a plurality of predefined shapes of the implant connector (e.g., after tolerated deformations of the implant connector).

The one or more reference positions may be determined based on a regression analysis of a plurality of pre-planned positions of implant interfaces. For example, the curve may be a regression line of a plurality of pre-planned positions of different implant interfaces. The curve may be a function fitted to the plurality of pre-planned positions of different implant interfaces, the function having a predefined maximum curvature. The regression line or the function may fulfil one or more predefined constraints so as to correspond to one of a plurality of predefined shapes of the implant connector (e.g., after tolerated deformations of the implant connector). For example, the regression line of the function may extend linearly within the predefined plane.

The pre-planned position of the at least one implant interface may be derived from a pre-planned pose (i.e., at least one of a position and an orientation) of the implant comprising the at least one implant interface. The at least one implant interface may have a predefined spatial relationship relative to the implant comprising the implant interface. The pre-planned position and/or the pre-planned pose may have been planned before a surgical procedure is started, for example based on pre-operative medical image data. Thus, the pre-planned position may be referred to as a position that was planned pre-surgery and the pre-planned pose may be referred to as a pose that was planned in advance of a surgery. The method may include the step of planning the pre-planned position and/or the pre-planned pose, for example before a surgical procedure is started.

The pre-planned position of the at least one implant interface or the pre-planned pose(s) of the implant(s) comprising the at least one implant interface may be patient-specific. The pre-planned position of the at least one implant interface or the pre-planned pose(s) of the implant(s) comprising the at least one implant interface may be defined relative to (e.g., pre-operative) medical image data of a patient. The pre-planned position of the at least one implant interface or the pre-planned pose(s) of the implant(s) comprising the at least one implant interface may be defined based on the (e.g., pre-operative) medical image data of the patient. The one or more reference positions may be defined relative to the (e.g., pre-operative) medical image data of the patient.

The method may further comprise obtaining the (e.g., pre-operative) medical image data representing at least one anatomical element of the patient. The method may comprise determining, based on the (e.g., pre-operative) medical image data and one or more predefined spatial requirements of the at least one anatomical element, alignment data indicative of a discrepancy of a pose of the at least one anatomical element from an anatomically correct pose of the at least one anatomical element patient. The one or more predefined spatial constraints may define one or more anatomically correct distances and rotations of the at least one anatomical element to other anatomical elements represented by the (e.g., pre-operative) medical image data, or may define an absolute (e.g., anatomically correct) pose of the at least one anatomical element.

The pre-planned position of the at least implant interface may be determined based on the alignment data. The method may further comprise obtaining placement data indicative of a predefined position of the at least one implant interface relative to the at least one anatomical element represented by the (e.g., pre-operative) medical image data. The method may comprise determining, based on the placement data and the alignment data, the pre-planned position of the at least one implant interface.

If the alignment data fulfils a first (e.g., set of) requirement(s), the predefined position may be used as the pre-planned position. For example, if the alignment data indicates a discrepancy falling below a predefined maximum discrepancy, the predefined position may be used as the pre-planned position.

If the alignment data fulfils a second (e.g., set of) requirement(s) or does not fulfil the first (e.g., set of) requirement (s), the predefined position may differ from the pre-planned position. In this case, the pre-planned position may be determined by changing (e.g., shifting or moving) the predefined position based on the alignment data (e.g., if the alignment data indicates a discrepancy falling above the predefined maximum discrepancy).

In case the at least one anatomical element comprises one or more vertebrae, the pre-planned position may be determined by (e.g., virtually) shifting the predefined position based on the alignment data, for example (e.g., only) if at least one of the following conditions is met: (i) a sagittal balance of a spine of the patient deviates from a neutral balance, (ii) an axial orientation of the vertebra (e.g., into which the implant comprising the at least one implant interface is to be implanted) deviates from an anatomically correct axial orientation, (iii) the spine of the patient has a scoliosis.

The indication may comprise a visual highlighting of a model of the at least one implant interface or of a model of the implant comprising the at least one implant interface. The visual highlighting may be representative of the deviation or the information derived from the deviation determined for the at least one implant interface.

The indication may comprise a visual highlighting of a virtual line connecting the at least one implant interface with another (e.g., an adjacent one) of the at least one implant interface. The visual highlighting may be representative of the deviation or the information derived from the deviation determined for the at least one implant interface or the another of the at least one implant interface.

The indication may comprise a visual highlighting or a visual element indicating at least one of (i) an amount and (ii) a direction of the deviation.

The information derived from the deviation may indicate whether the deviation meets a predefined criterion, for example whether the deviation exceeds a predefined threshold or indicates a misalignment in a predefined anatomical direction (e.g., in a lateral direction).

The visualization may be an augmented view. The visualization may be an augmented view in which the indication is overlaid onto at least a part of the patient's body or onto an image of at least a part of the patient's body. The visualization may be determined at least based on the (e.g., pre-operative) medical image data, the interface data and the reference data.

The first and the second implant may be of a same type (e.g., a bone screw). The at least one implant interface may comprise a screw head of a bone screw (e.g., a pedicle screw), the screw head configured to couple to a rod (e.g., a spinal rod) configured to connect the bone screw with another bone screw (e.g., another pedicle screw). The bone screw may be a polyaxial pedicle screw.

According to a second aspect, a system is provided. The system comprises a processor configured to perform a method for guiding a surgeon on how to adapt a pre-planned position of at least one implant interface, wherein the at least one implant interface (e.g., being part of a first implant) is configured to couple to an implant connector configured to connect the at least one implant interface with an implant interface of another (e.g., a second) implant. The processor is configured to obtain interface data indicative of a pre-planned position of at least one implant interface, and obtain reference data indicative of one or more reference positions of the at least one implant interface. The processor is configured to determine, based on the interface data and the reference data, a deviation between the pre-planned position of the at least one implant interface and the one or more reference positions, and trigger display of a visualization comprising an indication of the deviation or of information derived from the deviation, to guide a surgeon on how to adapt the pre-planned position of the at least one implant interface.

The processor may be configured to carry out the method according to the first aspect.

The system may further comprise an augmented reality device comprising a display. The processor may be configured to trigger display of the visualization on the display of the augmented reality device.

The system may further comprise a display unit. The processor may be configured to trigger display of the visualization by the display unit.

The system may further comprise a tracking system configured to track (e.g., a patient tracker fixedly attached relative to) a (e.g., the) patient's body and (e.g., a device tracker fixedly attached relative to) the augmented reality device to determine a relative pose between the patient's body and the augmented reality device.

According to a third aspect, a computer program is provided. The computer program comprises instructions which, when executed on at least one processor, cause the at least one processor to carry out the method according to the first aspect. The computer program may be stored on one or more (e.g., non-transitory) computer readable media. The computer program may alternatively be carried by a data stream. The computer program may be stored on a memory comprised in the system according to the second aspect.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
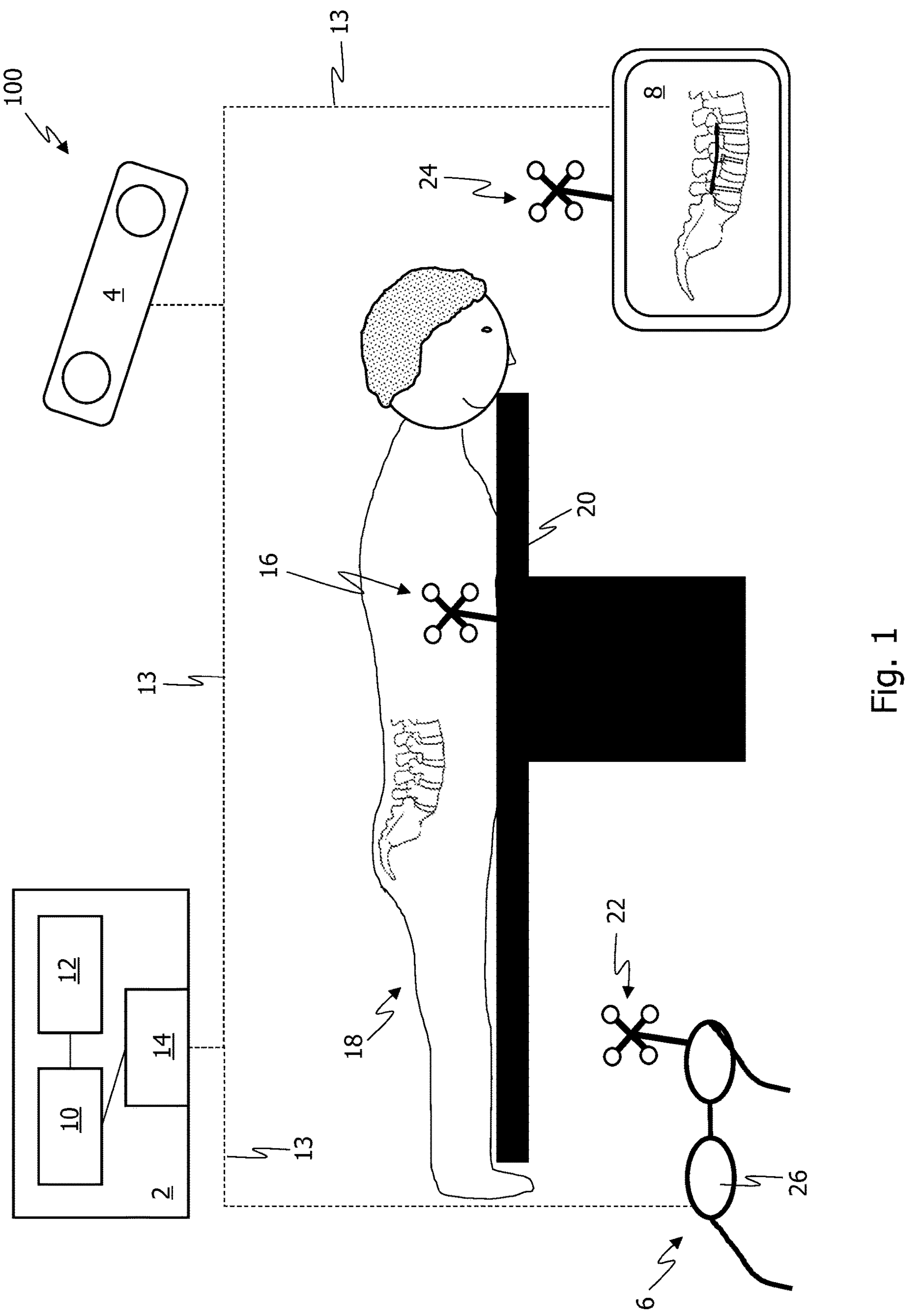
FIG. 1 shows a system in accordance with the present disclosure.

In the following description, exemplary embodiments of a system and a method will be explained with reference to the drawings. The same reference numerals will be used to denote the same or similar structural features.

FIG. 1 shows a system 100 in accordance with the present disclosure. The system 100 comprises a processing system 2, a tracking system 4, an augmented reality device (ARD) 6 and, optionally, a display unit 8.

The processing system 2 comprises a processor 10 coupled to a memory 12 and an interface 14. The memory 12 comprises instructions which, when executed by the processor 10, cause the processor 10 to perform the method disclosed herein. The processor 10 may communicate with the tracking system 4, the display unit 8 and the ARD 6 via one or more (e.g., wired or wireless) connections 13.

The tracking system 4 in the illustrated example is an optical tracking system comprising a stereo camera. The tracking system 4 may alternatively be an electromagnetic tracking system. The tracking system 4 is configured to track positions and orientations of a plurality of surgical trackers arranged within a field of view of the stereo camera. In the illustrated example, the tracking system 4 is configured to localize a patient tracker 16 that is fixed relative to a body 18 of a patient. The patient tracker 16 may be attached (e.g., glued) to the body 18 or to a patient support 20 carrying the body 18. The tracking system 4 is configured to localize a device tracker 22 attached to the ARD 6. The tracking system 4 may be configured to localize additional trackers such as a display tracker 24 attached to the display unit 8 and instrument trackers attached to surgical instruments such as a registration probe (not shown).

Based on the positions and orientations of the trackers 16, 22, 24, relative poses between the trackers can be determined. Medical image data of the patient may be registered to the body 18 based on a first registration, or transformation, between an image coordinate system of the medical image data and a tracking coordinate system of the tracking system 4, in particular a pose of the tracker 16 in the tracking coordinate system. The medical image data may be pre-operative image data of at least a part of the patient's body 18. Various techniques of determining the first registration are possible. As a non-limiting example, points on a surface of the body 18 may be acquired using the registration probe (not shown) tracked by the tracking system 4. The acquired points may then be matched to a body surface detected based on the medical image data to determine the first registration.

Other techniques of determining spatial relationships between the image data, the body 18, the ARD 6 and/or the display unit 8 are also possible. For example, the ARD 6 may comprise a depth sensor and a camera. A pose of the ARD 6 relative to the body 18 or relative to the tracking system 4 may be determined based on data acquired with the depth sensor and/or the camera. As another example, the tracking system 4 may track the body 18 directly, i.e., without tracking the patient tracker 16. In this case, the pose (i.e., at least one of a position and an orientation) of the body 18 may be determined by performing an image analysis of one or more images acquired by the (e.g., stereo) camera of the tracking system 4.

The ARD 6 comprises a display 26 (e.g., for each eye of a user). The display 26 may be configured as a see-through display or as a head-up display. Alternatively, the display 26 may be a non-transparent display configured to display an image acquired by the camera of the ARD 6. The display 26 is configured to provide a user, in particular a wearer, of the ARD 6 with an augmented view.

The display unit 8 may be part of a clinical workstation. In one example, the display unit 8 and the patient's body 18 are arranged in different rooms. The display unit 8 is configured as a non-transparent (e.g., non-see through) display. One or both of the display 26 and the display unit 8 are configured to display the visualization disclosed herein.

Figure 2:
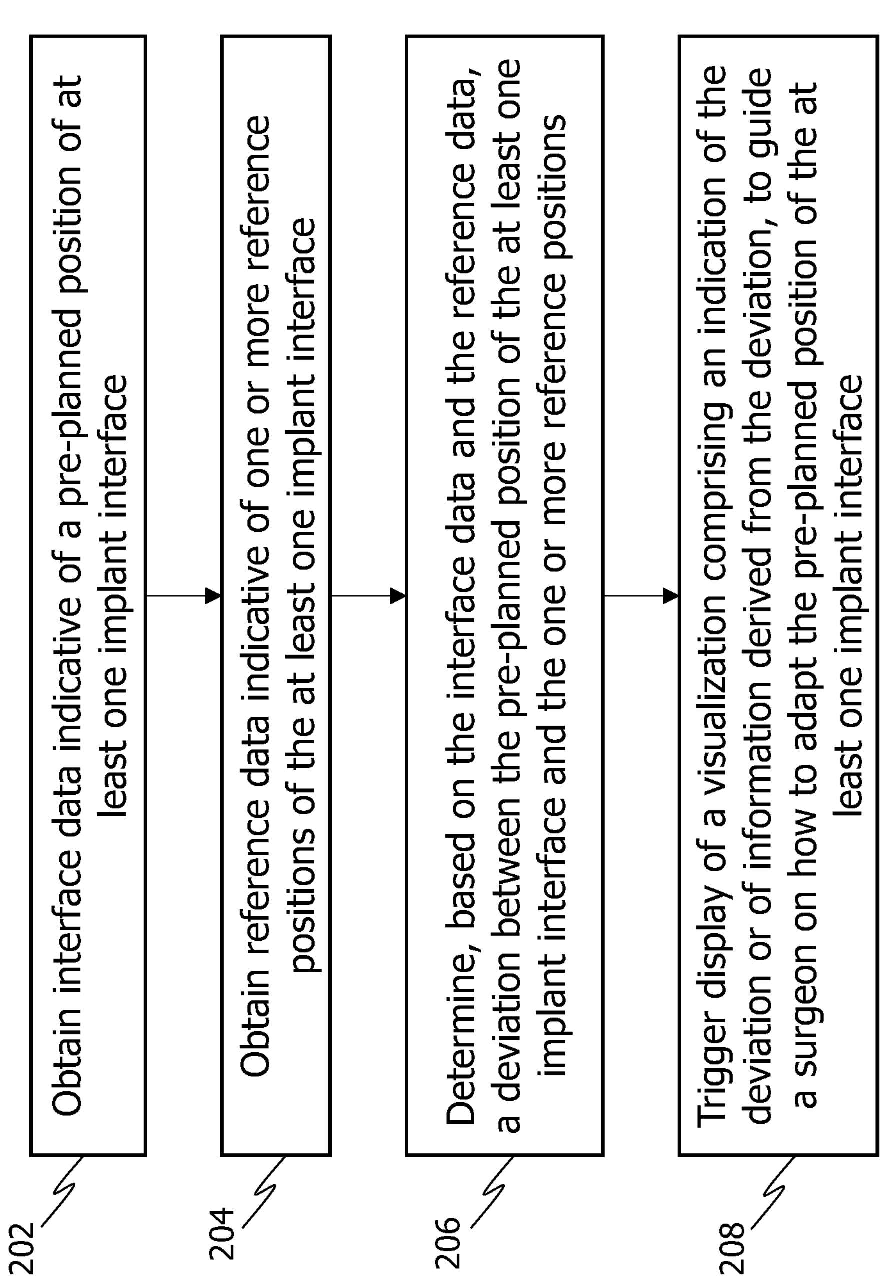
FIG. 2 illustrates a flowchart of a method in accordance with the present disclosure.

FIG. 2 illustrates a flowchart of a method in accordance with the present disclosure. The method may be performed by the processor 10.

In step 202, interface data indicative of a pre-planned position of at least one implant interface is obtained. The at least one implant interface is part of a first implant and is configured to couple to an implant connector configured to connect the at least one implant interface with an implant interface of a second implant.

For example, the implant may be a (e.g., poly-axial) pedicle screw and the implant interface may be a screw head of the pedicle screw configured to couple to a spinal rod. In this case, the implant connector corresponds to the spinal rod. As another example, the implant may be a bone screw and the implant interface may be a proximal end portion of the bone screw configured to couple to a screw hole of a bone plate. In this case, the implant connector corresponds to the bone plate. Other variants are also possible.

The pre-planned position of the at least one implant interface may be specific for the patient's body 18. The pre-planned position may be defined based on (e.g., pre-operative) medical image data of the patient. The (e.g., pre-operative) medical image data may comprise at least one type of image data chosen from computer tomography (CT) image data and magnetic resonance (MR) image data. The (e.g., pre-operative) medical image data may comprise one or more images of at least one anatomical element (e.g., at least one bone or organ) of the patient's body, wherein the first implant comprising the at least one implant interface is to be implanted into the at least one anatomical element.

The method may comprise obtaining the medical image data representing the at least one anatomical element (e.g., a vertebra) of the patient, and determining, based on the medical image data and one or more predefined spatial requirements of the at least one anatomical element, alignment data indicative of a deviation of a pose of the at least one anatomical element (e.g., as represented by the medical image data) from an anatomically correct pose of the at least one anatomical element (e.g., as defined by the one or more predefined spatial requirements). The one or more predefined spatial requirements may define anatomically correct distances and rotations of the at least one anatomical element to another anatomical element represented by the medical image data, or may define an anatomically correct position and orientation of the at least one anatomical element (e.g., in the image coordinate system).

Placement data indicative of a predefined position of the at least one implant interface relative to the at least one anatomical element represented by the medical image data may be obtained. For example, a surgeon may define a pose of the first implant, comprising the at least one implant interface, relative to a first anatomical element into which the first implant is to be implanted, the first anatomical element being represented by the medical image data of the patient. The placement data may then be derived from the defined pose of the first implant.

If the alignment data indicates that the pose of the at least one anatomical element deviates from its anatomically correct pose by an amount falling below a predefined maximum deviation, the predefined position may be used as the pre-planned position. In this case, one may say that the pre-planned position of the at least one implant interface may be defined relative to the medical image data. That is, the pre-planned position of the at least one implant interface may be defined relative to the at least one anatomical element (e.g., as represented by the medical image data) into which the implant comprising the at least one implant interface is to be implanted. That is, the pre-planned position of the at least one implant interface may correspond to a position of the at least one implant interface after placement of the implant and before adjustment of poses of the patient's anatomical elements. This may be advantageous if an alignment of the patient' anatomical elements toward anatomically correct poses does not change pre-planned positions of the implant interfaces relative to one another (e.g., at least in the coronal plane of the patient's body 18 or in a plane parallel to the coronal plane), for example in spinal fusion procedures of anatomically correctly aligned adjacent vertebrae (e.g., in case the patient does not have scoliosis).

One the other hand, if the alignment data indicates that the pose of the at least one anatomical element deviates from its anatomically correct pose by an amount falling above a predefined maximum deviation, the pre-planned position may be determined based on the predefined position and the alignment data, for example by shifting the predefined position based on the alignment data. The pre-planned pose of the at least one implant interface of the first implant to be implanted in the first anatomical element may correspond to the predefined position of the first implant interface after virtually shifting the first anatomical element into its anatomically correct pose based on the alignment data. One may say that in this case, the pre-planned position of the at least one implant interface may correspond to an estimated position of the at least one implant interface after placement of the respective implant and after correction of poses of the patient's anatomical elements into their anatomically correct poses. In other words, the pre-planned position of the at least one implant interface may correspond to an estimation in which position the at least one implant interface would be in case the anatomical elements of the patient's body 18 were in their anatomically correct poses. This approach may be advantageous if an alignment of poses of the patient's anatomical elements toward anatomically correct poses changes pre-planned positions of implant interfaces relative to one another (e.g., at least in the coronal plane of the patient's body 18 or in a plane parallel to the coronal plane), for example in spinal fusion procedures of anatomically incorrectly aligned vertebrae (e.g., in case the patient has scoliosis).

In step 204, reference data indicative of one or more reference positions of the at least one implant interface is obtained.

The reference data may be indicative of a curve or volume defining the one or more reference positions. The reference data may comprise a formula or parameters of a predefined formula defining a three-dimensional curve, wherein the one or more reference positions lie on the curve.

The one or more reference positions may be specific for at least one (e.g., the) implant connector (e.g., the spinal rod). The curve or volume may correspond to a shape of the implant connector. The implant connector may have a predefined shape defining the potential point(s) where the implant connector can couple to the implant interface(s), wherein each point corresponds to a reference position. The one or more reference positions may be specific for a plurality of implant connectors (e.g., different spinal rods), each of the plurality of implant connectors being configured to couple to the at least one implant interface. In this case, the one or more reference positions may lie in a volume comprising all potential attachment points on the plurality of implant connectors.

In a second variant, the one or more reference positions may be determined based on a regression analysis of a plurality of pre-planned positions of different implant interfaces. The regression analysis may be performed to obtain an approximate shape of an implant connector usable for connecting the plurality of implant interfaces. The individual pre-planned positions may then be compared with the approximate shape to determine the respective deviations. The regression analysis may be performed using predefined spatial constraints on the approximate shape of the implant connector (e.g., a maximum curvature of a regression function fitted to the pre-planned positions). The regression analysis may be performed based on projections of the plurality of pre-planned positions into a predefined plane (e.g., the coronal plane of the patient's body 18 as represented by the medical image data, or a plane parallel to the coronal plane). The curve may represent a function in the predefined plane that is fitted to the pre-planned positions. The curve may extend linearly in the predefined plane.

In step 206, based on the interface data and the reference data, a deviation between the pre-planned position of the at least one implant interface and the one or more reference positions is determined.

The deviation may be indicative of a spatial relationship between the pre-planned position of the at least one implant interface and exactly one of the one or more reference positions. The deviation may comprise or be a distance between the pre-planned position of the at least one implant interface and the exactly one of the one or more reference positions. The exactly one reference position may be a position on the curve, which is, among all other positions on the curve, closest to the pre-planned position. The deviation may comprise or be a distance between a projection of the pre-planned position of the at least one implant interface into the predefined plane and a projection of the exactly one of the one or more reference positions into the predefined plane. As mentioned above, the predefined plane may correspond to a coronal plane of the patient's body 18 or to a plane parallel to the coronal plane. In one example, the deviation comprises or is a smallest distance of distances between the pre-planned position of the at least one implant interface and the one or more reference positions (e.g., as defined by the curve or volume). The deviation may comprise or be a directional vector extending between the pre-planned position and the exactly one reference position or between the exactly one reference position and the pre-planned position. The deviation may be determined based on (e.g., as an average or median of) a plurality of distances between the pre-planned position and different ones (e.g., the closest ones) of the reference positions.

In step 208, a visualization comprising an indication of the deviation or of information derived from the deviation is triggered to be displayed, to guide a surgeon on how to adapt the pre-planned position of the at least one implant interface.

In a first example, the indication comprises a visual highlighting of a model of the at least one implant interface or of a model of the implant(s) comprising the at least one implant interface, wherein the visual highlighting is representative of the deviation or the information derived from the deviation determined for the at least one implant interface.

In a second example, the indication comprises a visual highlighting of a virtual line connecting the at least one implant interface with another of the at least one implant interface, wherein the visual highlighting is representative of the deviation or the information derived from the deviation determined for the at least one implant interface or the another of the at least one implant interface.

In a third example, the indication comprises a visual highlighting or a visual element indicating a direction of the deviation. The indication may comprise a visual highlighting (e.g., a color highlighting or a temporally varying, for example blinking, highlighting) or a visual element (e.g., a symbol, a text or a number) indicating an amount of the deviation.

The first, second and third examples may be combined. Other ways of indicating the deviation or the information derived from the deviation are also possible, for example using textual, numerical or graphical indications.

In one variant, the visualization is an augmented view. The indication may be visualized in an overlaid manner with the patient's body 18, in particular overlaid with the anatomical element into which the implant is to be placed. The augmented view may be determined based on the first registration between the image coordinate system and the tracking coordinate system, and based on a tracked pose of the ARD 6 relative to (e.g., in) the tracking coordinate system.

The visualization may inform the surgeon on critical deviations between (i) positions that implant interfaces will be in after placement of the implants (e.g., and after adjustment of the poses of the associated anatomical elements) and (ii) reference positions on the implant connector. This may guide the surgeon how to adapt the pre-planned pose(s) so as to avoid the critical deviations. The pre-planned pose of an implant interface may be adjusted by the surgeon, for example by changing a pose of the first implant relative to the first anatomical element represented by the medical image data of the patient's body 18. The surgeon may adjust the pre-planned position of the first implant interface by defining a new pose of the first implant in an image of the medical image data of the patient's body 18. The visualization may then be updated accordingly, informing the surgeon whether the adjustment was sufficient for avoiding the critical deviation(s) or not. That is, a feedback loop on the currently set pre-planned positions may be provided for the surgeon. In the end, the pre-planned positions may be defined such that the implants, after placement as defined by the pre-planned positions, extend into the respective anatomical elements, and such that the implant connector can couple to the implant interfaces without having to be deformed (e.g., above a predefined maximum curvature).

The method may further comprise triggering output of an audio signal representative of the deviation or of the information derived from the deviation. The audio signal may comprise a warning message or an alarm in case the deviation fulfils at least one predefined warning criterion (e.g., exceeds a predetermined maximum amount). The audio signal may be output by a speaker, for example a speaker comprised in the ARD 6.

Figure 3:
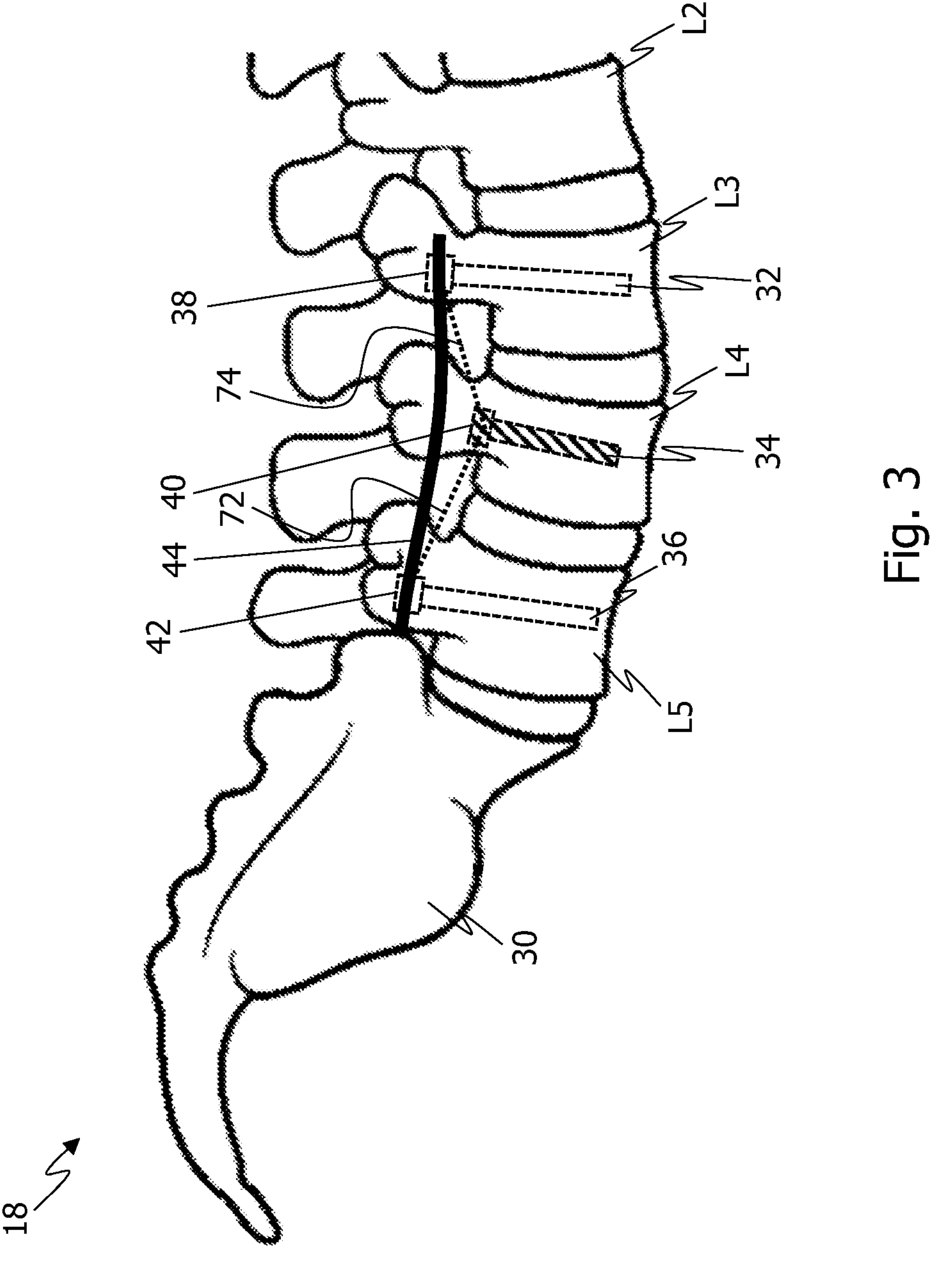
FIG. 3 illustrates an exemplary visualization in accordance with the present disclosure.

FIG. 3 is an exemplary visualization in accordance with the present disclosure. The visualization may be displayed on at least one of (i) the display 26 of the ARD 6 and (ii) the display unit 8 due to the visualization being triggered to be displayed in step 208.

In the visualization of FIG. 3, a plurality of anatomical elements are shown. In this example, four of the anatomical elements correspond to lumbar vertebrae L2-L5 of the patient's body 18 and one further anatomical element corresponds to the sacrum 30 of the patient's body 18, as represented by the medical image data of the patient's body 18. The visualization comprises a model of implants 32, 34, 36, each implant 32, 34, 36 being in a predefined pose (e.g., defined by the surgeon) relative to a respective vertebra L3, L4, L5 into which the implant 32, 34, 36 is to be inserted during surgery. The predefined pose of the implant 32, 34, 36 defines the predefined position of the respective implant interface 38, 40, 42. In the illustrated example, the spine has no scoliosis and, thus, no adjustment of the poses of the vertebrae L1-L5 in the predefined plane is required. Therefore, in this example, the predefined positions of the implant interfaces 38, 40, 42 correspond to the pre-planned positions thereof. The visualization further comprises a model of an implant connector 44 configured to connect the implants 32, 34, 36 to on another via the implant interfaces 38, 40, 42. The position and orientation of the implant connector 44 may be predefined by the surgeon or may be determined based on the pre-planned positions, for example by determining a pose of the spinal rod 44 in which the (i) deviations between the pre-planned positions and the reference positions on the spinal rod 44 are minimized, (ii) a minimum number of deviations falls below a predefined lower deviation (e.g., is null) or (iii) selected pre-planned positions (e.g., of the implant interfaces 38, 42) correspond to reference positions.

In the illustrated example, each implant is a pedicle screw and the implant connector is a spinal rod having a predefined shape. It can be seen that the implant interfaces 38, 42 lie on the spinal rod 44. In other words, the pre-planned positions of these two implant interfaces 38, 42 correspond to reference positions defined by the spinal rod 44. In this case, there is no deviation between the pre-planned positions of the implant interfaces 38, 42 and the reference positions as defined by the spatial extension of the spinal rod. On the other hand, the implant interface 40 of the implant 34 does not lie on the spinal rod 44. That is, there is a deviation between the pre-planned position of the implant interface 40 and the one or more reference positions as defined by the spinal rod 44. If the implants 32, 34, 34 were placed according to the pre-planned positions as shown in FIG. 3, it may not be possible to couple the rod 44 to the implant interface 40 without damaging the spinal cord due to a large movement of the vertebra L4 into the posterior direction relative to the adjacent vertebrae L3 and L5. Thus, the surgeon should not place the implants 32, 34, 36 in accordance with the pre-planned positions of the interfaces 38, 40, 42 as shown in FIG. 3.

The visualization shown in FIG. 3 guides the surgeon on how to adapt the pre-planned pose of the implant interface 40. In the illustrated example, the implant 34 comprising the implant interface 40 is highlighted (e.g., in a different color than the other implants 32, 36) to help the surgeon in identifying the instrument interface 40 which pre-planned position needs to be adjusted. Other warnings such as text or sound may be output for a similar purpose. The visualization in the illustrated example also comprises a model of the spinal rod 44 and of the implant interfaces 38, 40, 42, which helps the surgeon to understand into which direction the critical implant interface 40 should be moved to adjust the pre-planned pose thereof. Also shown are virtual connection lines 72, 74 between adjacent implant interfaces 38, 40 and 40, 42 (dashed lines in FIG. 3). The virtual connection lines 72, 74 may help a surgeon in understanding the amount and direction of the deviation of the instrument interface 40 from the reference positions.

Although FIG. 3 shows a view of the sagittal plane of the patient's body 18, the visualization is not limited thereto. The visualization may be a three-dimensional visualization, a view from the posterior direction, a view of the coronal plane, a view of the axial plane or the like. The visualization may be an augmented view. In this case, the contents shown in FIG. 3 may be displayed in an overlaid manner with the patient's body 18.

Figure 4:
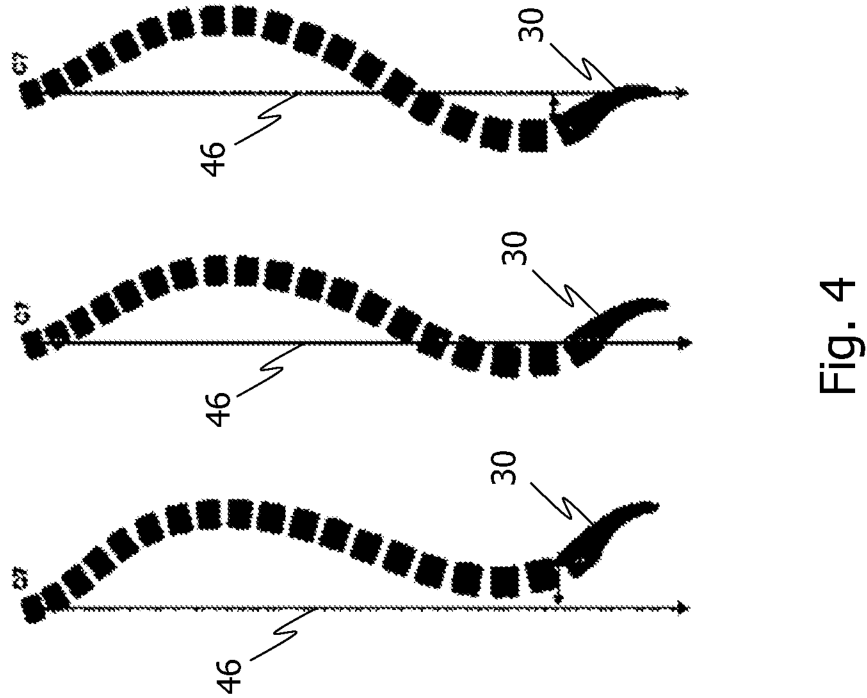
FIG. 4 illustrates a first technique for correcting poses of vertebrae.

FIG. 4 illustrates a first technique for correcting poses of vertebrae, in particular a technique of correcting a sagittal balance of the spine of the patient's body 18. The views shown in FIG. 4 are exemplary views of the sagittal plane of the patient's body 18.

In the leftmost illustration of FIG. 4, the spine of the patient has a positive balance, as the sacrum 30 is displaced in the proximal direction relative to a reference line 46 extending through (e.g., a center of) the vertebra C7. The reference line 46 may correspond to the intersection of the predefined (e.g., the coronal) plane and the sagittal plane of the patient's body 12. The positive balance may be adjusted by moving the sacrum into the anterior direction whilst maintaining the position of the vertebra C7. This adjustment may be performed virtually based on the medical image data, to determine the alignment data. This adjustment may only be performed if the proximal displacement of the sacrum 30 exceeds a predefined amount.

In the right illustration of FIG. 4, the spine of the patient has a negative balance, as the sacrum 30 is displaced in the anterior direction relative to the reference line 46. The negative balance may be adjusted by moving the sacrum into the posterior direction whilst maintaining the position of the vertebra C7. This adjustment may be performed virtually based on the medical image data, to determine the alignment data. This adjustment may only be performed if the anterior displacement of the sacrum 30 exceeds a predefined amount.

In the middle illustration of FIG. 4, the spine of the patient has a neutral balance. No adjustment of the sagittal balance of the spine may be performed in this case, and the predefined position of an implant interface may be taken as its pre-planned position.

The poses of the vertebrae of the spine as shown in the middle illustration of FIG. 4 may be used as anatomically correct (e.g., absolute) poses of vertebrae. Each vertebra of the patient as represented by the medical image data may be virtually shifted in space until it lies in its anatomically correct pose (e.g., if the proximal or anterior displacement of the sacrum 30 exceeds the predefined amount). The required displacement of the individual vertebrae may be used as the alignment data.

The pre-planned position(s) may correspond to position(s) of the respective implant interface(s) after the virtual adjustment of the balance of the patient's spine. In this case, the pre-planned position(s) of the implant interface(s) may be determined based on (i) the placement data indicative of the predefined position(s) relative to the (e.g., non-adjusted) vertebra(e) of the patient's body and (ii) the alignment data determined as described above. One may say that the predefined position(s) can be transformed into (e.g., shifted to) the pre-planned position(s) based on the alignment data.

Figure 5:
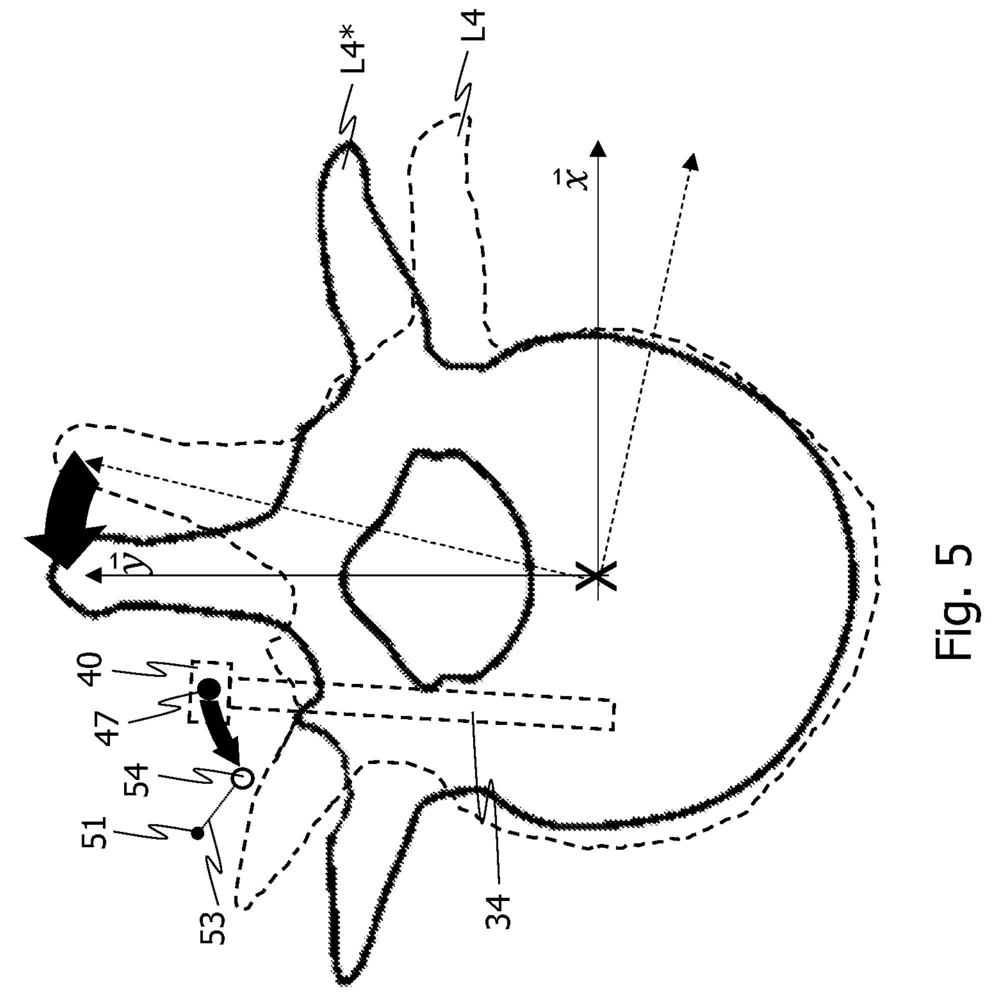
FIG. 5 illustrates a second technique for correcting poses of vertebrae.

FIG. 5 illustrates a second technique for correcting poses of vertebrae, in particular an axial orientation of the vertebrae. In FIG. 5, a pose of the vertebra L4 as represented by the medical image data is illustrated. The vertebra L4 has a center of mass denoted with the letter "X". A coordinate system of the vertebra L4 may be defined by using the center of mass as an origin and the distal end of the spinous process as the direction of the ordinate. Alternatively, X could be chosen as the center of the foramen. In this case, the coordinate system of the vertebra L4 may be defined by using the center of the foramen as an origin (and, e.g., the distal end of the spinous process as the direction of the ordinate).

In FIG. 5, the sagittal plane extends in the vertical direction. Thus, the pose of the vertebra L4 is rotated out of its anatomically correct orientation. The orientation of the vertebra L4 may be adjusted by virtually rotating the vertebra L4 as described by the medical image data around the origin of the coordinate system of the vertebra L4 (e.g., around a rotation axis extending in the superior-inferior direction and intersecting the point "X") until the ordinate of the coordinate system lies in the sagittal plane. The vertebra L4 after this rotation is illustrated as L4*. The alignment data may be indicative of this rotation performed to virtually correct the orientation of the vertebra L4. The direction of rotation is indicated with black arrows in FIG. 5.

The pre-planned position(s) may correspond to position(s) of the respective implant interface(s) after the virtual adjustment of the axial orientation of the vertebra(e) of the patient's spine. The pre-planned position(s) of the implant interface(s) may be determined based on (i) the placement data indicative of the predefined position(s) relative to the (e.g., non-adjusted) vertebra(e) of the patient's body and (ii) the alignment data determined as described above. The predefined position 47 of the implant interface 40 is illustrated in FIG. 5 with a dot. The predefined position 47 is defined relative to the non-adjusted vertebra L4. The pre-planned position 54 of the same implant interface 64 is illustrated in FIG. 5 with a circle. The pre-planned position 54 of the implant interface 64 corresponds to the predefined position 47 after the adjustment of the axial orientation of the vertebra L4 as indicated by the black arrow. The pre-planned position 54 may be defined relative to the adjusted vertebra L4*.

Also indicated in FIG. 5 is a reference position 51, and a deviation 53 of the pre-planned position 54 from the reference position 51. The deviation 53 may be divided into a first deviation in the anterior-posterior direction (e.g., in $\vec{y}$-coordinates of the coordinate system of the adjusted vertebra L4*) and into a second deviation in the lateral-medial direction (e.g., in $\vec{x}$-coordinates of the coordinate system of the adjusted vertebra L4*). The visualization may include an indication of at least one of the first deviation and the second deviation. In one particular example, the visualization may include an indication of only the second deviation. This may be sufficient in case the patient does not have scoliosis (e.g., in case the second deviation of each pre-planned position is smaller than a predefined threshold).

The reference position 51 may lie on a curve 50. As will be discussed below, the curve may correspond to a regression line determined based on a plurality of pre-planned positions including the pre-planned position 52. Alternatively, the reference position 51 may lie on a curve or line which shape is defined by an implant connector such as the spinal rod 44.

Figures 6A, 6B, 6C:
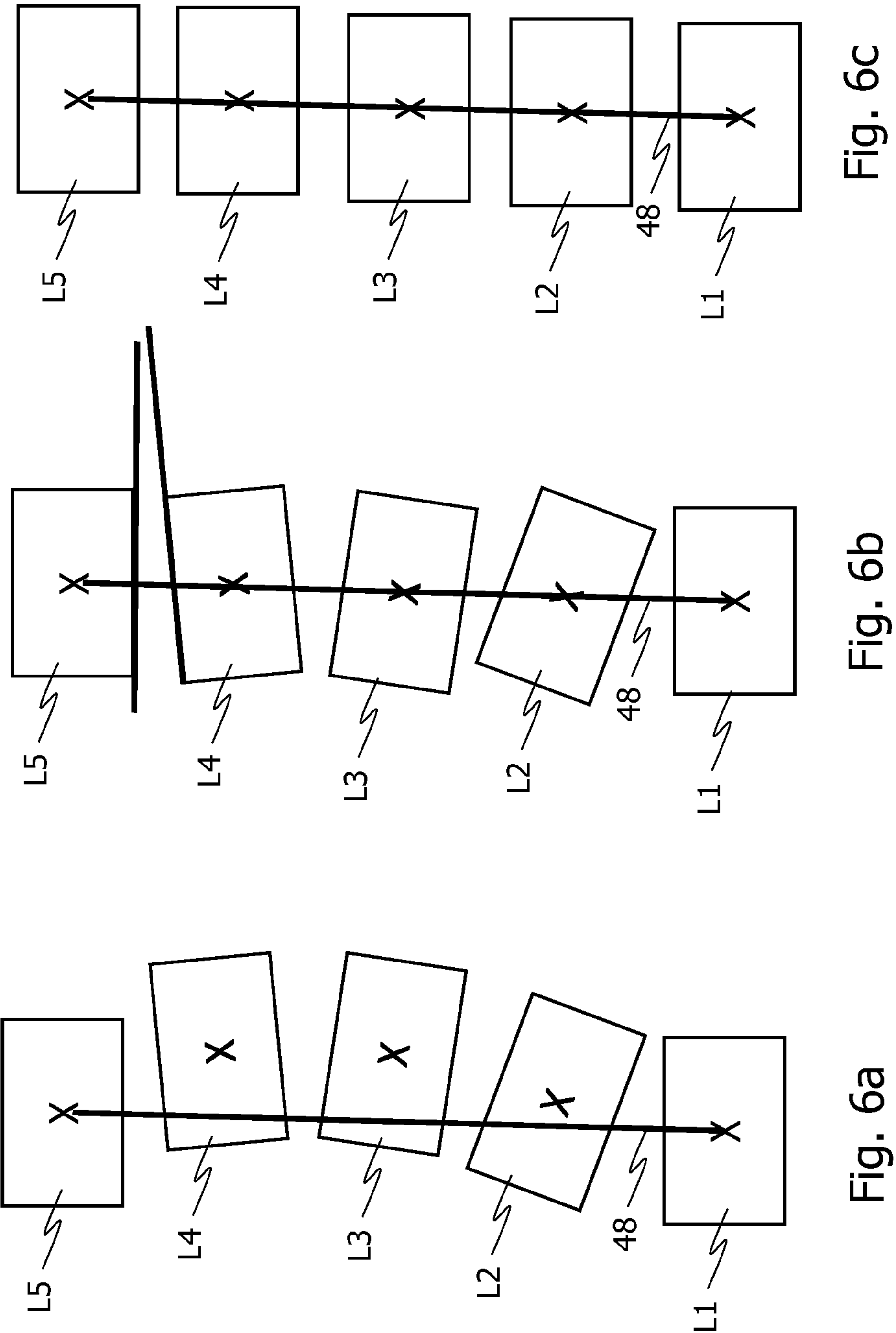
FIG. 6*a*-6*c* illustrate a third technique for correcting poses of vertebrae.

FIG. 6*a*-6*c* illustrate a third technique for correcting poses of vertebrae. The views shown in FIGS. 6*a* to 6*c* are schematic views of the spine of the patient's body 18 as viewed from a posterior direction. Although lumbar vertebrae L1-L5 are illustrated, the same technique may be used for other vertebrae of the patient's body 18. Each of the vertebrae L1-L5 has a center of mass indicated by the letter "X".

As apparent from FIG. 6*a*, the patient may have scoliosis. In this case, the positions of the center of mass of adjacent vertebrae deviate in the lateral directions. That is, only some of the centers of mass lie in the sagittal plane. The poses of the vertebrae may then need to be corrected by surgery. The pre-planned positions of the implant interface(s) may correspond to positions in which the implant interface(s) will lie after the poses of the vertebrae have been adjusted surgically. The method disclosed herein does not include a surgical step. To determine the pre-planned positions, the poses of the vertebrae may be virtually adjusted such that the vertebrae lie in their correct anatomical positions, as described in the following.

In a first step shown in FIG. 6*a*, a reference line 48 may be determined in the predefined plane. The reference line 48 may also lie in the sagittal plane and/or correspond to the reference line 46 described above. The reference line 48 may extend through the center of mass of an uppermost vertebra L1 and the center of mass of a lowermost vertebra L5 represented by the medical image data of the patient's body 18.

In a second step, the positions of the vertebrae L2-L4 are moved in the lateral direction such that the center of mass of each vertebra L1-L5 lies on the reference line 48 (e.g., at least when viewed from the posterior direction). Thereby, the vertebrae L1-L5 may all be aligned in the sagittal plane, but may still be tilted relative to one another when viewed from the posterior direction (see FIG. 6*b*).

In a third step, the orientation of each vertebra is adjusted by tilting the respective vertebra in the predefined plane around its center of mass (i.e., around an axis parallel to the sagittal and the axial plane of the patient's body and extending through the vertebra's center of mass). For example, the vertebra L4 may be tilted such that a caudal surface of the vertebral body of the vertebra L4 is parallel to a cranial surface of the vertebra L5 that neighbors the vertebra L4 in the caudal direction. One may say that the vertebrae can be aligned by detecting axial surfaces of the vertebral bodies and rotating the vertebrae in the predefined plane around the respective center of mass such that after the alignment all detected axial surfaces are parallel when viewed in from the posterior direction. The result of this adjustment of the orientations of the vertebrae L1-L5 is illustrated in FIG. 6*c*. The poses of the vertebrae L1-L5 as indicated in FIG. 6*c* may correspond to anatomically correct poses of the vertebrae L1-L5. A surgery for correcting the scoliosis of the patient's spine may be performed such that the vertebrae L1-L5 are in the poses as shown in FIG. 6*c*. Again, it is noted that the method described herein does not include a surgical step. The pre-planned positions of the implant interfaces may be defined relative to the vertebrae L1-L5 as shown in FIG. 6*c*, i.e., after the virtual adjustment of the poses of the vertebrae L1-L5. The alignment data may define the displacements and/or rotations of the individual vertebrae from the poses of the vertebrae as represented by the medical image data into the anatomically correct poses as shown in FIG. 6*c*. As noted above, the pre-planned position(s) of the implant interface(s) may be determined based on (i) the placement data indicative of the predefined position(s) relative to the (e.g., non-adjusted) vertebra(e) of the patient's body and (ii) the alignment data.

Figure 7C:
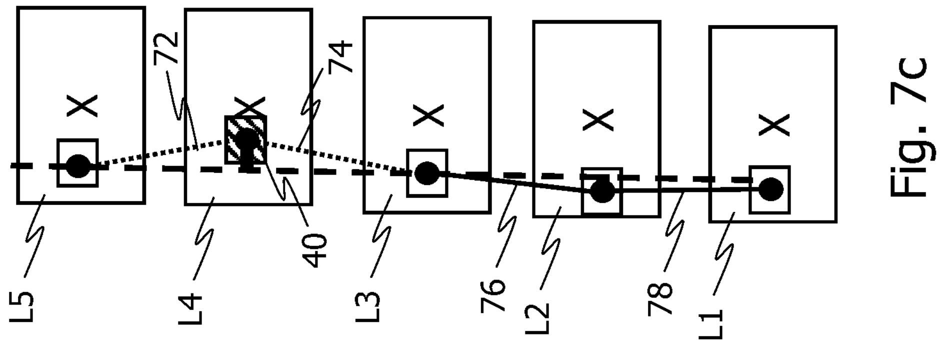
FIGS. 7*a*-7*c* schematically illustrate method steps and visualizations in accordance with the present disclosure.
Figure 7B:
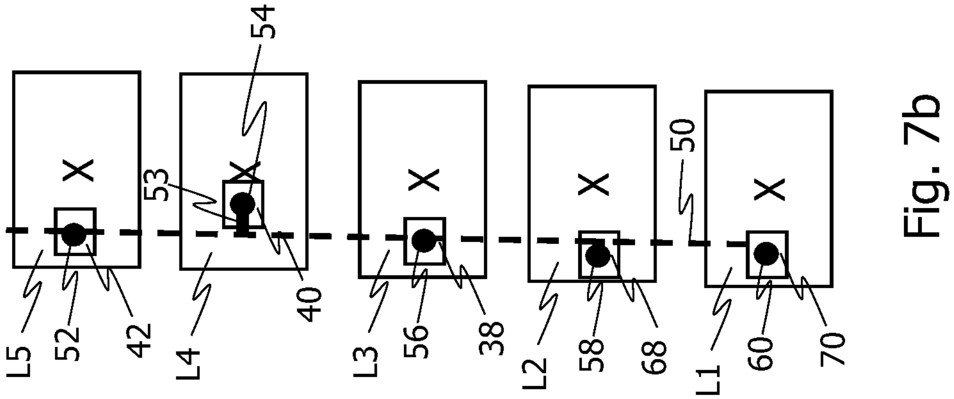
Figure 7A:
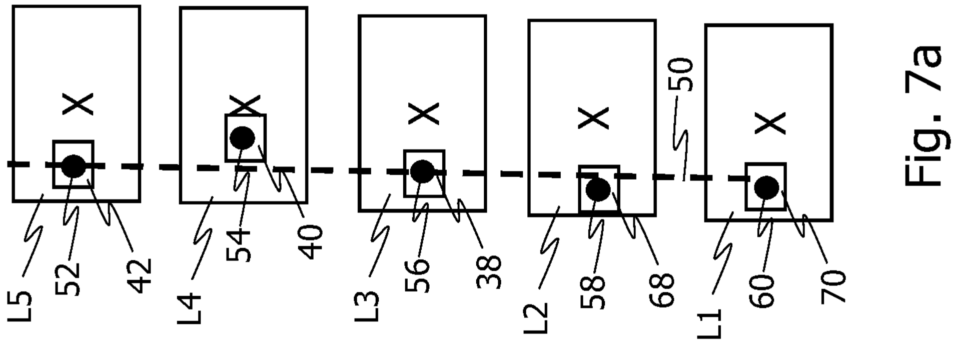

FIGS. 7*a*-7*c* schematically illustrate method steps and visualizations in accordance with the present disclosure.

FIG. 7*a* represents the virtually aligned plurality of anatomical elements of FIG. 6*c*, again viewed from the posterior direction. It is noted that in some scenarios, the medical image data may represent the vertebrae as shown in FIG. 7*a*, i.e., no scoliosis may be present. In this case, the correction of poses of the vertebrae as discussed above with reference to FIGS. 6*a*-6*c* may not need to be performed, and the pre-planned positions may be readily defined in one or more images of the (e.g., raw, original, unadjusted or unaligned) medical image data. Optionally, the correction of poses of vertebra discussed for FIGS. 4 and/or 5 may be performed to determine the pre-planned positions.

In FIG. 7*a*, the center of mass of each vertebra L1-L5 is indicated with the letter "X" and the pre-planned positions 52, 54, 56, 58, 60 of a plurality of implant interfaces 38, 40, 42, 68, 70 are indicated with black dots. In this example, each implant interface 38, 40, 42, 68, 70 belongs to another pedicle screw and each pedicle screw shall be implanted in another vertebra L1-L5.

The curve 50, in this example a straight line, is determined based on a regression analysis of all pre-planned positions 52, 54, 56, 58, 60 of the implant interfaces 38, 40, 42, 68, 70. One may say that the curve 50 represents a function fitted to the pre-planned positions 52, 54, 56, 58, 60 (e.g., at least in the predefined plane). In an alternative implantation, the curve 50 represents a shape of a spinal rod (e.g., the rod 44) that is to be coupled to the implant interfaces 38, 40, 42, 68, 70. All points that lie on the curve 50 correspond to reference positions, including the reference position 51. The visualization may comprise a representation of the reference positions (e.g., may visualize the curve 50).

As shown in FIG. 7*b*, a smallest distance of each pre-planned position 52, 54, 56, 58, 60 to the curve 50 is determined as a measure of the deviation between the respective pre-planned position 52, 54, 56, 58, 60 and the reference positions. The deviation of the pre-planned position 54 of the implant interface 40 from the reference position(s) is indicated by reference sign 53 in FIG. 7*b*. The visualization may comprise lines connecting the respective pre-planned position 52, 54, 56, 58, 60 with the curve 50, the lines indicating to the shortest distance between the pre-planned position 52, 54, 56, 58, 60 and the reference positions, (e.g., the bold horizontal line in FIG. 7*b* marked with reference sign 53). Each line may be color-coded depending on the length of the respective line, thereby for example visually highlighting all lines that are longer than a predetermined maximal length (e.g., a predetermined maximal deviation between an implant interface and a spinal rod).

The visualization may alternatively or additionally comprise connective lines 72, 74, 76, 78 between implant interfaces 38, 40, 42, 68, 70 of implants to be implanted into adjacent vertebrae, as illustrated in FIG. 7*c*. The connective lines 72, 74 ending at the implant interface 40, the pre-planned position of which is farther from the curve 50 than a predefined maximal distance (e.g., a predetermined maximal distance between an implant interface and a spinal rod), may be visualized differently than the other connective lines 76, 78. The implant interface 40, the pre-planned position of which is farther from the curve 50 than the predefined maximal distance, may be visualized differently than (i.e., distinguishably from) the other implant interfaces 38, 42, 68, 70.

The surgeon may, when provided with the visualization, adjust the pre-planned position 54 of the implant interface 40 such that it is closer to the curve 50. Upon adjustment of the pre-planned position, the visualization may be (e.g., continuously) updated, providing the surgeon with feedback on the effect of the performed adjustment on the alignment of the implant interface 40 relative to the other implant interfaces 38, 42, 68, 70. That is, the visualization guides the surgeon on how to adapt the pre-planned position 54 such that the deviation 53 thereof is minimized (e.g., falls below the predefined maximal distance).

It is noted that in case a scoliosis is present, the visualization may not visualize the corrected poses of the vertebrae L1-L5 as shown in FIGS. 6*c*-7*c*, but may instead reproduce the orientations as represented by the medical image data (see for example FIG. 6*a*). Still, the deviations may be determined based on the alignment data and the placement data. This may enable providing the surgeon with an augmented view informing the surgeon on the respective deviations determined based on the pose correction(s) described above.

The technique disclosed herein may provide a surgeon with a visualization that guides him in adjusting a pre-planned pose of an implant interface, such that the pre-planned pose complies with spatial constraints imposed by an implant connector to which the implant interface shall be coupled. The pre-planned pose may either be defined in medical image data (e.g., in case no scoliosis is present) of a patient, or may be determined by virtually shifting a pose of an anatomical element, relative to which a predefined position is defined, the anatomical element being represented by the medical image data, into an anatomically correct pose. The predefined pose after the virtual shifting may then be used as the pre-planned pose. This may allow estimating a position of the implant interface after correction of poses of the anatomical element(s) of the patient and ensure that these estimated positions comply with the spatial constraints imposed by the implant connector. In other words, positions in which the implant interfaces will be after surgery can be estimated in advance of the surgery, and can then be adjusted in advance of the surgery, such that the implant interfaces can be coupled to the implant connector when performing the surgery later on. This may allow using pre-shaped implant connectors and obviate the need to deform the implant connector during surgery. Furthermore, the technique disclosed herein may ensure that implant interfaces can be coupled to the implant connector during surgery without causing harm to the patient or the implant connector. The technique presented herein may thus not only be expedient for the surgeon, but also improve clinical outcome. Further advantages of the present disclosure may be apparent to those skilled in the art.

The invention claimed is:

1. A method for guiding a surgeon on how to adapt a pre-planned position of at least one implant interface, wherein the at least one implant interface is configured to couple to an implant connector configured to connect the at least one implant interface with an implant interface of another implant, the method performed by a processing system and comprising:

obtaining interface data indicative of a pre-planned position of at least one implant interface;

obtaining reference data indicative of one or more reference positions of the at least one implant interface, wherein the one or more reference positions are determined based on a regression analysis of a plurality of pre-planned positions of implant interfaces;

determining, based on the interface data and the reference data, a deviation between the pre-planned position of the at least one implant interface and the one or more reference positions; and triggering display of a visualization comprising an indication of the deviation or of information derived from the deviation, to guide a surgeon on how to adapt the pre-planned position of the at least one implant interface.

2. The method of claim 1, wherein the deviation is indicative of a spatial relationship between the pre-planned position of the at least one implant interface and exactly one of the one or more reference positions.

3. The method of claim 2, wherein the deviation comprises or is a distance between the pre-planned position of the at least one implant interface and the exactly one of the one or more reference positions.

4. The method of claim 2, wherein the deviation comprises or is a distance between a projection of the pre-planned position of the at least one implant interface into a predefined plane and a projection of the exactly one of the one or more reference positions into the predefined plane.

5. The method of claim 3, wherein the deviation comprises or is a smallest distance of distances between the pre-planned position of the at least one implant interface and the one or more reference positions.

6. The method of claim 1, wherein the reference data is indicative of a curve or volume defining the one or more reference positions.

7. The method of claim 1, wherein the one or more reference positions are specific for the implant connector.

8. The method of claim 6, wherein the curve or volume corresponds to a shape of the implant connector.

9. The method of claim 1, wherein the pre-planned position of the at least one implant interface is defined relative to or based on medical image data of a patient.

10. The method of claim 9, further comprising:

obtaining the medical image data representing at least one anatomical element of the patient; and determining, based on the medical image data and one or more predefined spatial requirements of the at least one anatomical element, alignment data indicative of a discrepancy of a pose of the at least one anatomical element from an anatomically correct pose of the at least one anatomical element, wherein the pre-planned position of the at least one implant interface is determined based on the alignment data.

11. The method of claim 10, further comprising:

obtaining placement data indicative of a predefined position of the at least one implant interface relative to the at least one anatomical element; and determining, based on the placement data and the alignment data, the pre-planned position of the at least one implant interface.

12. The method of claim 1, wherein the indication comprises a visual highlighting of a model of the at least one implant interface or of a model of an implant comprising the at least one implant interface, wherein the visual highlighting is representative of the deviation or the information derived from the deviation determined for the at least one implant interface.

13. The method of claim 1, wherein the indication comprises a visual highlighting of a virtual line connecting the at least one implant interface with another of the at least one implant interface, wherein the visual highlighting is representative of the deviation or the information derived from the deviation determined for the at least one implant interface or the another of the at least one implant interface.

14. The method of claim 1, wherein the indication comprises a visual highlighting or a visual element indicating a direction of the deviation.

15. The method of claim 1, wherein the visualization is an augmented view.

16. The method of claim 1, wherein the at least one implant interface comprises a screw head of a bone screw, the screw head configured to couple to a rod configured to connect the bone screw with another bone screw.

17. A system comprising a processor configured to perform a method for guiding a surgeon on how to adapt a pre-planned position of at least one implant interface, wherein the at least one implant interface is configured to couple to an implant connector configured to connect the at least one implant interface with an implant interface of another implant, the processor configured to:

obtain interface data indicative of a pre-planned position of at least one implant interface;

obtain reference data indicative of one or more reference positions of the at least one implant interface, wherein the one or more reference positions are determined based on a regression analysis of a plurality of pre-planned positions of implant interfaces;

determine, based on the interface data and the reference data, a deviation between the pre-planned position of the at least one implant interface and the one or more reference positions; and trigger display of a visualization comprising an indication of the deviation or of information derived from the deviation, to guide a surgeon on how to adapt the pre-planned position of the at least one implant interface.

18. The method of claim 1, wherein the pre-planned position of the at least one implant interface is planned before a surgical procedure for implanting an implant comprising the at least one implant interface is performed.

19. A non-transitory computer-readable medium storing a computer program comprising instructions which, when executed on at least one processor, cause the at least one processor to:

obtain interface data indicative of a pre-planned position of at least one implant interface;

obtain reference data indicative of one or more reference positions of the at least one implant interface, wherein the one or more reference positions are determined based on a regression analysis of a plurality of pre-planned positions of implant interfaces;

determine, based on the interface data and the reference data, a deviation between the pre-planned position of the at least one implant interface and the one or more reference positions; and trigger display of a visualization comprising an indication of the deviation or of information derived from the deviation, to guide a surgeon on how to adapt the pre-planned position of the at least one implant interface.

* * * * *